United States Patent
Zaleski

Patent Number: 5,993,408
Date of Patent: Nov. 30, 1999

[54] THIN TIP PHACO NEEDLE

[75] Inventor: Edward R. Zaleski, Santa Ana, Calif.

[73] Assignee: Allergan Sales, Inc., Irvine, Calif.

[21] Appl. No.: 08/943,472

[22] Filed: Oct. 3, 1997

[51] Int. Cl.[6] .................................................. A61B 17/20
[52] U.S. Cl. ............................ 604/22; 604/272; 604/294; 606/166; 606/223
[58] Field of Search ............................. 604/22, 272, 273, 604/274, 283, 902, 294; 606/107, 161, 166, 171, 223

[56] References Cited

U.S. PATENT DOCUMENTS

| | | |
|---|---|---|
| 4,169,984 | 10/1979 | Parisi . |
| 4,689,040 | 8/1987 | Thompson ................................. 604/22 |
| 4,816,018 | 3/1989 | Parisi . |
| 5,084,009 | 1/1992 | Mackool . |
| 5,112,339 | 5/1992 | Zelman . |
| 5,154,694 | 10/1992 | Kelman . |
| 5,213,569 | 5/1993 | Davis ........................................ 604/22 |
| 5,242,385 | 9/1993 | Strukel . |
| 5,286,256 | 2/1994 | Mackool . |
| 5,772,667 | 6/1998 | Blake ....................................... 606/107 |

*Primary Examiner*—Wynn Wood Coggins
*Assistant Examiner*—LoAn H. Thanh
*Attorney, Agent, or Firm*—Walter A. Hackler

[57] ABSTRACT

A thin tip phaco needle is provided including a body having a longitudinal bore for enabling passage of debris from a surgical site, a threaded end for engaging an ultrasonic probe handpiece, and a tip, disposed at a distal end of the body, for cutting tissue. The tip includes a beveled, or stepped, edge having a wide proximal wall and a thin, distal, cutting wall of about half a width of the wide wall. The beveled edge functions to enhance cutting efficiency of the tip and increase force pressure by the tip on tissue such as to decrease ultrasonic energy required to cause the needle to penetrate hard tissue. The needle tip may be angled so as to define a cutting plane having a wide upper arc and a thin lower arc.

15 Claims, 1 Drawing Sheet

THIN TIP PHACO NEEDLE

The present invention generally relates to ultrasonic surgical instruments and more specifically relates to a thin tip needle suitable for phacoemulsification surgery.

In modern surgical practice, many procedures which formerly required large incisions have been replaced by techniques employing microsurgical tools which can be inserted through a relatively small incision and perform a variety of surgical functions therein. For example, prior to the development of microsurgical tools, cataract removal surgery on an eye involved excising a diseased lens by means of a 180° incision about the lens which was thereafter removed intact in order to prepare the eye for the insertion of an artificial replacement lens.

In contrast, phacoemulsification, which involves utilization of a handheld microsurgical tool, is currently one of the most commonly used techniques for removing a diseased lens. The microsurgical tool, known as a phacoemulsification handpiece, or probe, generally includes a small diameter needle with a tip which may be designed for emulsifying, fragmenting and/or cutting tissue after it is inserted in an incision in the cornea or sclera of the eye. In addition, the needle typically includes a central channel connected to a source of suction which aspirates the tissue debris from the eye. The handpiece may include lumens for supplying an irrigation fluid, such as a saline solution, to the eye for flushing the eye during the procedure. The excised tissue which is aspirated from the eye along with irrigation fluid is collected in a collection vessel of some type, usually located remote from the handpiece. Thus, the phacoemulsification handpiece typically will perform multiple tasks through a single, small incision.

A control console, remote from the handpiece, is provided which typically includes a source of suction for the aspirating function of the surgical tool, connections to a source of irrigation fluid for the irrigation function of the handpiece, as well as power for driving the cutting or emulsifying aspect of the needle tip. Ultrasonic power to the needle may be controlled by footpedal operation in order to free the surgeon's hands during the surgery.

In an attempt to provide better performance of the phacoemulsification probe, a variety of needle types have been developed. A standard phacoemulsification needle has an annular cutting edge with a wall cross section of about 0.003 to about 0.004 inches to maintain sufficient strength for withstanding ultrasound movement. In order to increase sharpness, the needle tip may be angled to define a wedge shaped edge.

During a surgical procedure, when the needle tip encounters tissue which requires additional cutting force, for example in the case of hard cataracts, power to the needle may be increased. The increase in ultrasonic power will increase force pressure on a contact area between the needle tip and the tissue. Naturally, an increase in ultrasonic power will result in more powerful vibrations within the eye which may be damaging to more sensitive eye tissue. It is generally accepted that the application of ultrasonic energy during phacoemulsification surgery should be minimized in power and duration to reduce the risk of damage.

SUMMARY OF THE INVENTION

Accordingly, it is an object of the present invention to provide a phacoemulsification needle having improved cutting ability over conventional devices without additional ultrasonic energy being applied to the needle. This is provided by a thin tip phaco needle having a cutting edge cross section of less than approximately half a cutting edge cross section of a conventional needle. Moreover, the geometry of the needle tip of the present invention is maintained constant throughout the life of the needle. In other words, despite the exceptional fineness of the needle tip, the geometry of the needle tip provides sufficient strength to resist breakage during use.

A thin tip phaco needle, in accordance with the present invention, generally comprises a body having a longitudinal bore for enabling passage of cut tissue therethrough. Means, disposed at a proximal end of said body are provided for engaging an ultrasonic probe handpiece. The present invention also comprises a tip, disposed at a distal end of the body, for cutting tissue. Importantly, the tip includes chamfer means for enhancing cutting efficiency of the tip.

More particularly, the chamfer means may be comprised of a beveled or stepped cutting edge of the tip, having a wide proximal wall and a thin distal wall, said thin distal wall having a cross section of about half of a cross section of the wide proximal wall.

Even more particularly, the thin wall of the beveled or stepped cutting edge is exceptionally fine and has a generally uniform cross section of between about 0.0005 and 0.0015 inches. The thin wall has a full length of approximately 0.005 inches extending from a distal most point of the needle tip.

The tip of the needle may have a needle angle of between about 10 degrees to about 60 degrees. The needle angle is measured from a perpendicular with respect to the needle axis. When the needle angle is greater than zero degrees, the beveled or stepped cutting edge is disposed only on a lower arc of the needle tip.

Importantly, as will be discussed in detail hereinafter, the structure of the needle of the present invention greatly enhances the cutting ability thereof over conventional phaco needles. The needle tip of the present invention is substantially sharper than a conventional needle tip, providing for increased force pressure on a smaller contact area.

BRIEF DESCRIPTION OF THE DRAWINGS

The advantages of the present invention will be more clearly understood with reference to the following detailed description when considered in conjunction with the appended drawings of which.

DETAILED DESCRIPTION

Figure 1:
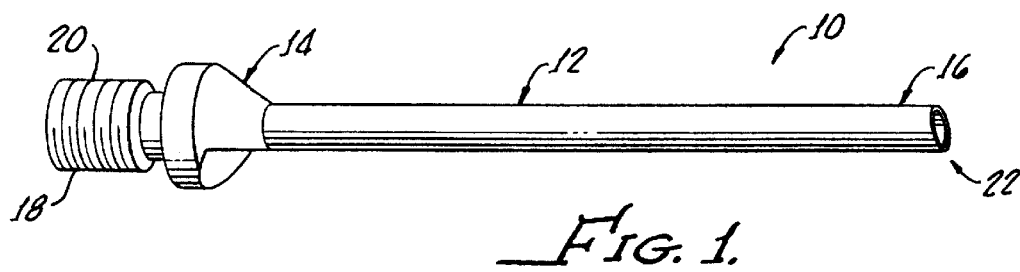
FIG. 1 shows a perspective view of a thin tip phacoemulsification needle in accordance with the present invention.

Turning now to FIG. 1, a phacoemulsification needle 10 in accordance with the present invention is shown. The needle 10 comprises, generally, a body 12, having a proximal end 14 and a distal end 16. Means 18, disposed at the proximal end 14 of the body 12, are provided for engaging in a conventional manner, an ultrasonic handpiece (not shown). For example, the proximal end 14 may include threads 20 for enabling screwing of the needle 10 onto a reciprocating portion of the handpiece (not shown). The needle 10 further comprises a tip 22, disposed at the distal end 16 of the body 12.

Figures 2, 3:
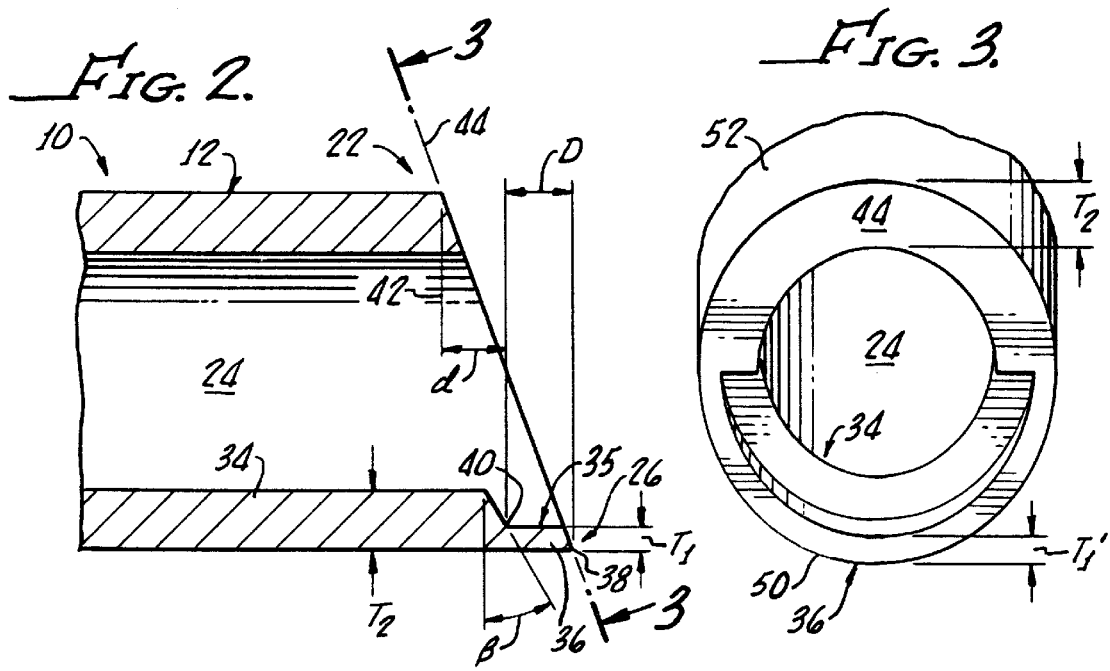
FIG. 2 shows, in cross sectional view, a beveled or stepped distal cutting edge of the phacoemulsification needle of FIG. 1.
FIG. 3 shows a front plane view of the cutting edge taken along line 3—3 in FIG. 2.

FIG. 2 shows a cross sectional view of the tip 22, and a portion of the body distal end 16. As shown, aspiration means, defined by a longitudinal bore 24 through said body portion 12 and tip portion 22 is provided for enabling passage of cut tissue through the needle 10 such that tissue debris and fluids may be removed from the surgical site in a conventional manner, for example, by a remote source of suction.

Importantly, the needle tip 22 includes a chamfer structure 26 which provides means for enabling the needle 10 to penetrate increasingly harder tissue without an increase in energy supplied thereto. More particularly, the chamfer structure 26 provides for increased cutting efficiency of the tip 22, and more specifically comprises a beveled or stepped structure 26, including an arcuate distal portion 35 having an inner surface coaxial with respect to the needle longitudinal axis, which enable easy severing of hard tissue (not shown), for example, cataract tissue, in an eye.

More particularly, the chamfer means 26 may include a wide proximal wall 34 and a thin distal wall 36, the thin distal wall 36 having a cross section $T_1$ that is about half of a cross section $T_2$ of the wide proximal wall 34. For example, the wide proximal wall cross section $T_2$ may be about 0.003 inches, which as will be discussed hereinafter, is comparable to a conventional needle wall cross section.

Even more particularly, the thin distal wall 36 has a cross section $T_1$ of between about 0.0005 inches and about 0.0015 inches in width, and is preferably about 0.0015 inches. The thin wall 36 cross section $T_1$ has a length D wherein D is measured from a distal most needle edge 38 to a point 40 of inception of the wide wall 34. In other words, the arcuate distal portion has a length D, wherein D is a length from about 0.005 inches to about 0.033 inches.

Preferably, the tip 22 has a needle angle of greater than zero degrees (0°). The needle angle is represented in FIG. 2 as an angle $\alpha$, defined as the angle between a cutting plane of the needle to a line 42 perpendicular to the needle, the cutting plane represented as line 44. More preferably, the needle angle $\alpha$ is between about 10° and about 60° and even more preferably is about 30°.

When the needle angle ($\alpha$) is greater than zero degrees, the chamfer structure 26 is disposed only along a lower arc 50 of the needle tip 22 as shown. This may be more clearly understood with reference to FIG. 3. In this example, the tip 22 defines a generally annular cutting plane 44 having a thin lower arc 50 having width $T_1'$ and a wide upper arc 52 having width $T_2'$ which may be about twice the width of the thin lower arc width $T_1'$.

Referring now back to FIG. 2, the wide wall 34 preferably forms an angle $\beta$ greater than zero degrees with respect to the perpendicular line 42. More particularly, wide wall angle $\beta$ may be equal to about 60°.

As shown in FIG. 2, the chamfer structure 26 defines a tip 22 having an angular cutting edge that is extremely sharp, burr free and exhibits no light reflection from the edge upon 10× magnification. Despite this fineness of the needle tip 22 in accordance with the present invention, it will resist breakage and maintain constant edge geometry throughout the life thereof.

Figure 4:
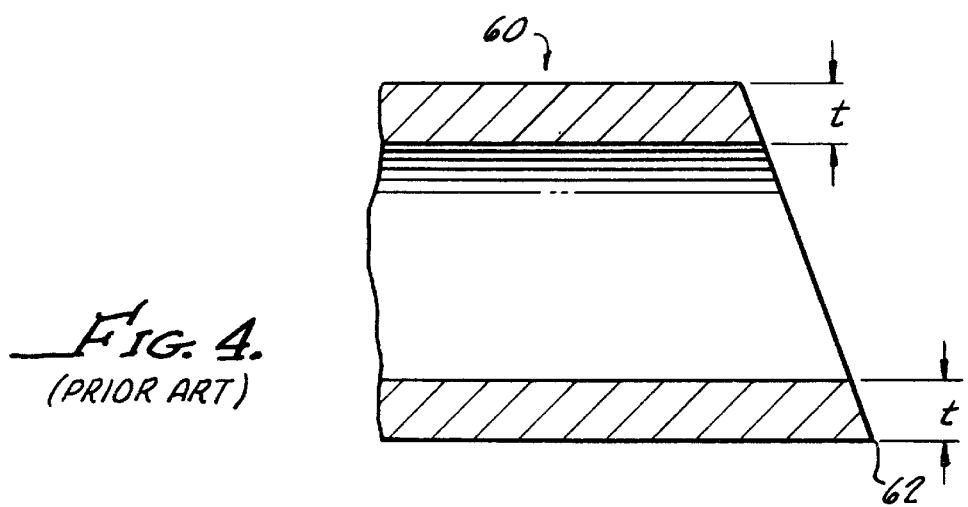
FIG. 4 shows, in cross sectional view, a typical prior art phacoemulsification needle tip for use in phacoemulsification surgery.

A standard, conventional phacoemulsification needle 60, more particularly a tip 62 thereof, is shown in FIG. 4, and typically has a uniform wall cross section "t" of from about 0.003 to about 0.004 inches to maintain sufficient strength for withstanding ultrasound movement. As discussed hereinabove, when a physician encounters hard tissue during surgery using such a conventional phaco needle 60, an increase in mechanical or electrical energy to the phaco needle is required to sever or emulsify the hard tissue. Such an increase in energy increases risk of damage to healthy surrounding tissues. However, it is well known that a single diseased cataract tissue typically varying degrees of hardness, thus frequently necessitating a fluctuation of applied energy to the needle during surgery.

One way to decrease this risk of injury is to design a needle tip having, a smaller area of contact between the needle edge and the tissue, thus allowing the needle to cut through the tissue with less applied force. This approach has been taken conventionally, as shown in FIG. 4, by angling the needle tip so that it defines a sharp distal tip 62 rather than a flat, zero degree annular cutting plane. Although an angled needle tip has greater cutting efficiency than a zero degree needle tip because an initial area of contact with the tissue will tend to be smaller, it is does not decrease an overall surface area of the cutting plane, which must eventually penetrate the tissue. Prior to the present invention, attempts to decrease the area of the cutting plane by decreasing the cross section t have been unsuccessful because strength of the needle tip was compromised when the tip was designed thinner than about 0.003 to 0.004 inches.

Advantageously, the design of the present invention described hereinabove, including the wide proximal wall adjacent the thin distal wall, has overcome this problem by providing a fine tip needle which resists breakage, even though the cutting edge may have a width of only about 0.0015 inches or less.

Although there has been hereinabove described a thin tip phaco needle in accordance with the present invention for the purposes of illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defined in the appended claims.

What is claimed is:

1. An ultrasonic probe needle comprising:
   a needle body having a longitudinal axis and including means, defined by a longitudinal bore, for enabling passage of cut tissue therethrough;
   means, disposed at a proximal end of said needle body, for engaging an ultrasonic probe handpiece;
   tip means, disposed at a distal end of said needle body, for cutting tissue, said tip means including chamfer means, defined by a wide proximal wall and a thin distal wall, defining a sharp angular cutting edge for enhancing cutting efficiency of the tip means, said chamfer means including an arcuate distal portion having an inner surface coaxial with respect to the longitudinal axis.

2. The ultrasonic probe needle according to claim 1 wherein the arcuate distal portion has a width of between about 0.0005 inches and 0.0015 inches.

3. The ultrasonic probe according to claim 2 wherein the arcuate distal portion has width of about 0.0015 inches.

4. The ultrasonic probe needle according to claim 2 wherein the arcuate distal portion has a length from about 0.005 inches to about 0.033 inches.

5. The ultrasonic probe needle according to claim 1 wherein the tip means has a needle angle of between about 10° and about 60°.

6. The ultrasonic probe needle according to claim 5 wherein the needle angle is about 30°.

7. The ultrasonic probe needle according to claim 5 wherein the wide proximal wall defines an angle of about 60° with respect to a line perpendicular to the longitudinal axis of the needle body.

8. An ultrasonic probe needle comprising:
   a needle body including means, defined by a longitudinal bore, for enabling passage of cut tissue therethrough;
   means, disposed at a proximal end of said needle body, for engaging an ultrasonic probe handpiece;
   tip means, disposed at a distal end of said needle body, for cutting tissue, said tip means including a chamfer structure having a wide proximal wall and a thin distal wall, said thin distal wall defining a sharp, angular cutting edge of the needle body.

9. The ultrasonic probe needle according to claim 8 wherein the thin distal wall has a width of between about 0.0005 and about 0.0015 inches.

10. The ultrasonic probe needle according to claim 9 wherein the thin distal wall has a width of about 0.0015 inches.

11. The ultrasonic probe needle according to claim 9 wherein the wide proximal wall is spaced apart from the thin distal wall a length of between about 0.005 inches to about 0.033 inches.

12. The ultrasonic probe needle according to claim 8 wherein the tip means has a needle angle of between about 10° and about 60°.

13. The ultrasonic probe needle according to claim 12 wherein the needle angle is about 30°.

14. The ultrasonic probe needle according to claim 12 wherein the tip means defines a generally annular cutting plane having a thin lower arc and a wide upper arc wherein said thin lower arc is about half a width of the wide upper arc.

15. An ultrasonic probe needle comprising:
   a body including means, defined by a longitudinal bore, for enabling passage of cut tissue therethrough;
   means, disposed at a proximal end of said body, for engaging an ultrasonic probe handpiece;
   tip means, disposed at a distal end of said body, for cutting tissue, said tip means including a needle angle of about 30°, and chamfer means for enhancing cutting efficiency of the tip means and increasing force pressure by the tip means on the tissue, said chamfer means including a wide proximal wall having a cross section of at least about 0.003 inches, and a thin distal wall defining a sharp cutting edge having a cross section of between about 0.0005 to about 0.0015 inches and a length of about 0.005 inches, said wide proximal wall disposed at an angle of about 60° with respect to a line perpendicular to the needle, and said tip means defining a cutting plane having a thin lower arc and a wide upper arc.

* * * * *